United States Patent [19]
Koike et al.

[11] Patent Number: 6,015,921
[45] Date of Patent: Jan. 18, 2000

[54] PROCESS FOR PRODUCING CARBAMOYLMETHYLUREA DERIVATIVES

[75] Inventors: Haruo Koike, Souraku-gun; Yasufumi Ueda, Tokushima; Koji Matsuda, Kobe; Mikio Kabaki, Ashiya, all of Japan

[73] Assignee: Shionogi & Co., Ltd., Osaka, Japan

[21] Appl. No.: 09/000,147

[22] PCT Filed: Jul. 25, 1996

[86] PCT No.: PCT/JP96/02078

§ 371 Date: Feb. 3, 1998

§ 102(e) Date: Feb. 3, 1998

[87] PCT Pub. No.: WO97/06135

PCT Pub. Date: Feb. 20, 1997

[30] Foreign Application Priority Data

Aug. 7, 1995 [JP] Japan .................................. 7-200749

[51] Int. Cl.⁷ ........................ C07C 229/34; C07C 231/02
[52] U.S. Cl. ..................... 560/36; 564/48; 564/138; 564/139
[58] Field of Search ............................. 560/36; 564/48, 564/138, 139

[56] References Cited

U.S. PATENT DOCUMENTS

| | | | |
|---|---|---|---|
| 2,928,873 | 3/1960 | Shapiro et al. | 260/553 |
| 5,475,106 | 12/1995 | Bourzat et al. | 544/58.4 |
| 5,739,162 | 4/1998 | Hagishita et al. | 514/534 |

FOREIGN PATENT DOCUMENTS

| | | |
|---|---|---|
| 5-504970 | 7/1993 | Japan . |
| 5504967 | 7/1993 | Japan . |

OTHER PUBLICATIONS

Papadopoulas, J. Heterocyclic Chem., 18, 515–518, 1981.

*Primary Examiner*—Shailendra Kumar
*Attorney, Agent, or Firm*—Foley & Lardner

[57] ABSTRACT

A method for preparing carbamoylmethylurea derivatives of the formula (I):

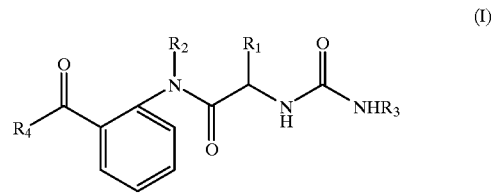

characterized by reacting a compound of the formula (II):

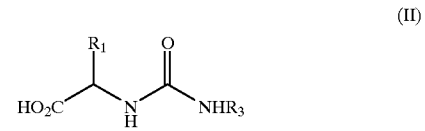

with a compound of the formula (III):

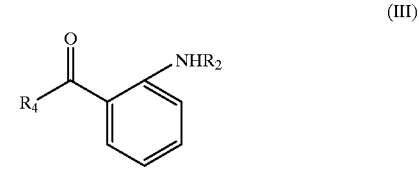

5 Claims, No Drawings

PROCESS FOR PRODUCING CARBAMOYLMETHYLUREA DERIVATIVES

FIELD OF THE INVENTION

The present invention relates to a method for preparing carbamoylmethylurea derivatives having an activity of competing with gastrin and/or cholecystokinin and are useful as an active ingredient of a medicine, and intermediates therefor and the preparation thereof.

BACKGROUND OF THE INVENTION

Gastrin and cholecystokinin (CCK) are physiologically active substances belonging to the gastrointestinal peptide hormone family, which exert various functions by interacting with receptors. Receptors for gastrin are mainly present in parietal cells of fundic glands and those for the latter are classified in two types, i.e., peripheral type (CCK-A receptors) present in peripheral tissues such as digestive gut and central type (CCK-B receptors) present in brain. Inhibitors of such peptide hormones are expected to be useful for preventing and/or treating various disorders caused by the effect of the hormones on digestive gut and/or central nervous system. To achieve an effective prevention and/or treatment, it is necessary to use a compound capable of binding to an aimed peptide hormone receptor in preference, discriminating it from receptors for peptide hormones of different sub-type. For instance, gastrin antagonists specific to gastrin receptors are thought to be effective on gastrin-associated disorders such as peptic ulcers in gaster and duodenum, Zollinger-Ellison syndrome, hyperplasia of sinus G cells, and decrease in gastrin activity. (Taisha, 29/7, 1992, R. Eissele, H. Patberg, H. Koop, W. Krack, W. Lorenz, A. T. McKnight & R. Arnold, Gastroenterology, 103, 1596 (1992), etc.) Antagonists specific to CCK-B receptors are thought to be useful in the reinforcement and elongation of the analgetic effect of opioid-type compounds (e.g., morphine derivatives such as morphine sulfate or hydrochloride) which competitively bind to opioid receptors [Drugs of the future 18, 919 (1993); Proc. Natl. Acad. Sci. U.S.A., Vol. 87, p. 71, 05 Sep. 1990, Neurobiology].

The present applicant has developed certain carbamoylmethylurea derivatives which have selective and potent affinity for gastrin- and/or CCK-B-receptors but have low affinity for CCK-A receptors (WO95/21856). The carbamoylmethylurea derivatives are represented by the formula (I):

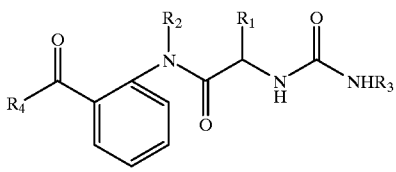

(I)

wherein $R_1$ is a hydrogen or lower alkyl; $R_2$ is a hydrogen or —$CH_2COR_5$ ($R_5$ is lower alkoxy, lower alkylamino, cycloalkyl, optionally substituted phenyl or optionally substituted heterocyclic group); $R_3$ is an optionally substituted phenyl; $R_4$ is an optionally substituted phenyl, optionally substituted cycloalkyl, optionally substituted alkyl or optionally substituted heterocyclic group. Compounds wherein $R_2$ is —$CH_2COR_5$ have especially potent pharmacological activity and are useful as anti-ulcer agent, and those wherein $R_2$ is hydrogen is also useful as an intermediate.

For the clinical application of the compounds (I) in the treatment and prevention of various diseases, it is essential to establish a measure for supplying them stably. However, conventional preparation methods such as those described in WO91/12264, U.S. Pat. No. 5,223,529, WO91/12265, WO91/13907, WO91/13874, WO91/13862, WO93/01167, WO94/15914, WO94/15955 involve complicated procedures including protection of aromatic carboxyl group, deprotection, etc., and are not suited for the industrial production of the compounds (I). Accordingly, there has been a strong demand for the development of a method which affords the compounds (I) more efficiently and simply, thereby contributing to the establishment of stable supply of the compounds (I), and also to the clinical application thereof.

SUMMARY OF THE INVENTION

The present invention solves the problems above and provides a method for preparing carbamoylmethylurea derivatives of the formula (I), which comprises reacting a carboxymethylurea derivative of the formula (II):

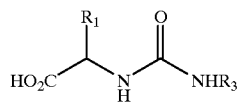

(II)

wherein $R_1$ is a hydrogen or lower alkyl; and $R_3$ is an optionally substituted phenyl, or a reactive derivative thereof with an aniline derivative of the formula (III):

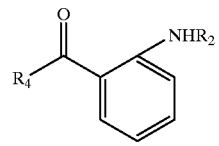

(III)

wherein $R_2$ is a hydrogen or —$CH_2COR_5$ ($R_5$ is lower alkoxy, lower alkylamino, cycloalkyl, optionally substituted phenyl or optionally substituted heterocyclic group); and $R_4$ is an optionally substituted phenyl, optionally substituted cycloalkyl, optionally substituted alkyl or optionally substituted heterocyclic group. The present invention also provides the compounds (II) and (III) which are used as a starting compound, and the preparation thereof.

The terms used in the definition of compound (I) are defined below.

The term "alkyl" means straight or branched chain $C_1$–$C_{10}$ hydrocarbon group including nonyl and decyl in addition to lower alkyl as defined below.

The term "lower alkyl" means straight or branched chain $C_1$–$C_8$ hydrocarbon group including methyl, ethyl, n-propyl, i-propyl, n-butyl, s-butyl, t-butyl, n-pentyl, i-pentyl, neopentyl, s-pentyl, t-pentyl, n-hexyl, neohexyl, i-hexyl, s-hexyl, t-hexyl, heptyl and octyl, and $C_1$–$C_3$ hydrocarbon group is preferred.

The term "cycloalkyl" means $C_3$–$C_7$ cycloalkyl group including cyclopropyl, cyclobutyl, cyclopentyl, cyclohexyl and cycloheptyl, and $C_3$–$C_5$ cycloalkyl group is preferred.

The term "lower alkoxy" means straight or branched chain $C_1$–$C_6$ alkoxy group including methoxy, ethoxy, n-propoxy, i-propoxy, n-butoxy, s-butoxy, t-butoxy, n-pentyloxy, i-pentyloxy, neopentyloxy, s-pentyloxy, t-pentyloxyr n-hexyloxy, neohexyloxy, i-hexyloxy, s-hexyloxy and t-hexyloxy. Preferred alkoxy is $C_1$–$C_4$ alkoxy, in particular t-butoxy.

The term "lower alkylamino" means an amino group substituted by above-defined lower alkyl, including methylamino, ethylamino, n-propylamino, i-propylamino, n-butylamino, t-butylamino, and the like.

The term "heterocyclic group" means 5- to 7-membered both aromatic- and non-aromatic heterocyclic groups containing one or more hetero atoms selected independently from the group consisting of O, S and N. Examples of aromatic heterocyclic group include furyl, thienyl, tetrazolyl, pyrrolyl, pyrazolyl, imidazolyl, oxazolyl, thiazolyl, pyridinyl, and triazinyl. Examples of non-aromatic heterocyclic group include pyrrolidinyl, thiazolidinyl, oxazolidinyl, imidazolidinyl, thiazolinyl, oxazolinyl, imidazolinyl, piperidinyl, piperadinyl, morpholinyl, thiomorpholinyl, oxadiazolyl, oxadinyl and dioxanyl.

Preferred heterocyclic groups are, in the case of $R_5$, pyrrolidinyl and morpholinyl, and in the case of $R_4$, those containing N-atom, especially, piperidinyl optionally protected with amino-protecting group.

In the definition of $R_5$, the term "optionally substituted phenyl" means a phenyl which may be substituted by 1–3 substituents selected from, for example, amino, hydroxy, halogen, lower alkyl and halogenated lower alkyl, at ortho-, metha- and/or para-position.

The term "halogen" means bromine, chlorine, fluorine or iodine.

In the definition of $R_5$, the term "optionally substituted heterocyclic group" means a heterocyclic group which may be substituted by 1–3 substituents selected from, for example, amino, hydroxy, halogen, lower alkyl and halogenated lower alkyl.

In the definition of $R_3$, the term "optionally substituted phenyl" means a phenyl which may be substituted by a substituent(s) selected from, for example, halogen, cyano, lower alkoxy, lower alkyl, halogenated lower alkyl, —$R_5$—($CH_2$)n—$R_7$ [$R_6$ is a bond, —O—, —S—, —S(O)— or —S(O)$_2$—, $R_7$ is an aromatic heterocyclic group or —COOR$_8$ ($R_8$ is a hydrogen, lower alkyl, lower alkenyl, or aralkyl), n is an integer of 0 to 3], $NO_2$, $NH_2$, OH, SMe, $CONH_2$, $OCF_3$, $CH_2CN$, $CH_2OH$, $CH_2OMe$, $CH_2NH_2$, and the like, preferably —COOR$_8$. The substituent(s) may be at the ortho-, metha- and/or para-position.

The term "aralkyl" means an alkyl group substituted by aryl group, including benzyl, phenylethyl, methylbenzyl, naphtylmethyl, and the like. Benzyl is especially preferred.

In the definition of $R_4$, the term "optionally substituted phenyl", "optionally substituted alkyl", "optionally substituted heterocyclic group" or "optionally substituted cycloalkyl" means each group which may be substituted by 1–3 substituents selected from, for example, electron attracting- or releasing-groups such as amino, hydroxy, halogen, lower alkyl, halogenated lower alkyl and lower alkoxy. The substituent(s) may be at the ortho-, metha- and/or para-position.

The term "halogenated alkyl" or "halogenated lower alkyl" means an alkyl or lower alkyl group as defined above which is substituted by one or more, preferably 1–3 halogen atom(s), including —$CF_3$, —$CHF_2$—, —$CH_2F$—, —$CH_2CCl_3$—, —$CH_2CHClCH_3$—, and the like.

THE MOST PREFERRED EMBODIMENT FOR PRACTICING THE INVENTION

The present method will hereinafter be explained in more detail.

Both the carboxymethylurea derivatives (II) and aniline derivatives (III) useful as the starting materials for the present method can be prepared in accordance with any methods known in the art though, they can be obtained more efficiently in accordance with the novel method of the present invention as shown below.

(1) Carboxymethylurea derivatives (II) can be prepared by reacting a compound of the formula (IV):

wherein $R_3$ is as defined above, with a chlorocarbonate ester and allowing the product to react with a compound of the formula (V):

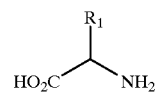

wherein $R_1$ is as defined above.

Chlorocarbonate ester is a compound having a partial structure "ClCOO—". Examples of chlorocarbonate ester include optionally substituted arylchloroformate (e.g., phenyl- chloroformate (ClCO$_2$Ph), ClCO$_2$Ph—NO$_2$), optionally substituted alkylchloroformate (e.g., ClCO$_2$Et, ClCO$_2$CH$_2$Ph), and the like. The optionally substituted aryl, in particular ClCO$_2$Ph (Ph is phenyl) is preferred in terms of mildness of reaction conditions.

The reaction between the compound (IV) and chlorocarbonate ester is carried out in the presence of a base such as hydroxide (NaOH), carbonate (Na$_2$CO$_3$) or bicarbonate (NaHCO$_3$) of alkali metal, or the like, in a solvent such as acetonitrile, water, or the like, at temperature range of –10 to 30° C., preferably –5 to 5° C. The amount of carbonate ester can generally be between 1.0 to 1.5 equivalents, preferably 1.0 to 1.3 equivalents of compound (IV) in molar ratio.

A compound (e.g., $R_3$—NHCO$_2$Ph) having a partial structure of "$R_3$NHCO$_2$—", which can be an intermediate of the reaction above is, when reacted, without isolation, with an amino acid derivative of the formula (V) in the same solvent at temperature range of about 0 to 100° C., preferably 40 to 70° C. for about 0.5 to 3 hours, converted into an intended carboxymethylurea derivative (II).

Protection and deprotection reactions can optionally be conducted in conventional manner using a known protecting group before and after the reaction above.

Thus, according to the method above, the compound (II) can be prepared from the starting compound (IV) in continuous reactions without isolating an intermediate.

(2) The another starting compound for the present method, aniline derivatives (III) wherein $R_2$ is —CH$_2$COR$_5$, can be prepared by reacting a compound of the formula (VI):

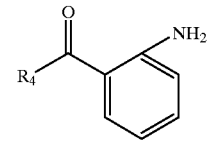

wherein $R_4$ is as defined above, with a compound (VII):

$$\underset{XCH_2CR_5}{\overset{O}{\|}}$$ (VII)

Wherein $R_5$ is as defined above and X is halogen. The reaction between a compound (VI) and a compound (VII) is carried out in the presence of an alkali such as carbonate salt ($K_2CO_3$, etc.) and, preferably, in the co-existence of alkali iodide (LiI, NaI, KI, etc.) in a solvent such as amide solvent (HMPA, DMA, DMF, etc.) or nitrile solvent (acetonitrile, etc.) at preferable temperature range of 50 to 100° C. The amount of each substance used in the reaction is, when expressed by molecular ratio to compound (VI), from 1 to 2 equivalents, preferably 1 to 1.5 equivalents for compound (VII), from 1 to 2 equivalents, preferably 1 to 1.5 equivalents for a base, and from 0.1 to 0.5 equivalents for alkali iodide, in general.

Protection and deprotection reactions can optionally be conducted in conventional manner using known protecting groups before and after the reaction above.

(3) Then, a carboxymethylurea derivative (II) and aniline derivative (III) prepared according to the methods (1) and (2) above or any methods known in the art are reacted by an amidation method.

The amidation reaction is generally carried out after converting a carboxymethylurea derivative (II) or aniline derivative (III) into a known reactive derivative(s), or in the presence of a suitable condensing agent. A suitable aprotic solvent such as ethyl acetate, dichloromethane, acetonitrile, or the like can be used.

The compound (II) is used in slightly excess, preferably 1.5 to 2 molar equivalents of the aniline compound (III).

The reaction is generally carried out at temperature range of about –50 to 50° C., preferably –30 to 10° C.

Condensing agent is preferably a combination of chlorination agent and N-substituted amide. Examples of chlorination agent include $SOCl_2$, $POCl_3$, and the like, and $SOCl_2$ is preferred. Examples of N-substituted amide include DMF (dimethylformamide), HMPA (hexamethylphosphoric triamide), DMA (dimethyl acetamide), and the like. These compounds can serve as not only a catalysis but also a solvent. The most preferred combination is $SOCl_2$ and DMF.

In the case of a compound (II) wherein $R_3$ is carboxy-substituted phenyl, the amidation could be confronted with the problem of selectivity between aliphatic- and aromatic carboxyl groups, which possibly results in the side-products and decrease of yield. This problem is avoidable by protecting an aromatic carboxylic group and deprotecting the same before and after the reaction.

However, according to the present method, where the amidation reaction is carried out in the presence of above-mentioned chlorination agent and N-substituted amide, the aliphatic carboxyl group of a compound (II) can be selectively amidated while leaving the aromatic carboxyl group free, under relatively mild reaction conditions.

The following examples are provided to further illustrate the present invention in detail, but they are only for illustrative purpose and are not to be construed as limiting the scope of the present invention.

The so produced compound (I) has proved to have an excellent characteristic as anti-ulcer agent in both in vivo and in vitro experiments. The present invention, which provides highly efficient method for preparing carbamoyl-methylurea derivatives (I) useful as a medicine, makes it possible to supply the said compounds stably, and thereby contributing to the improvement of the clinical application thereof. The useful effect of the method of the present invention could be further enhanced when combined with the method for preparing the novel starting compounds, which also fall within the scope of the invention.

EXAMPLE

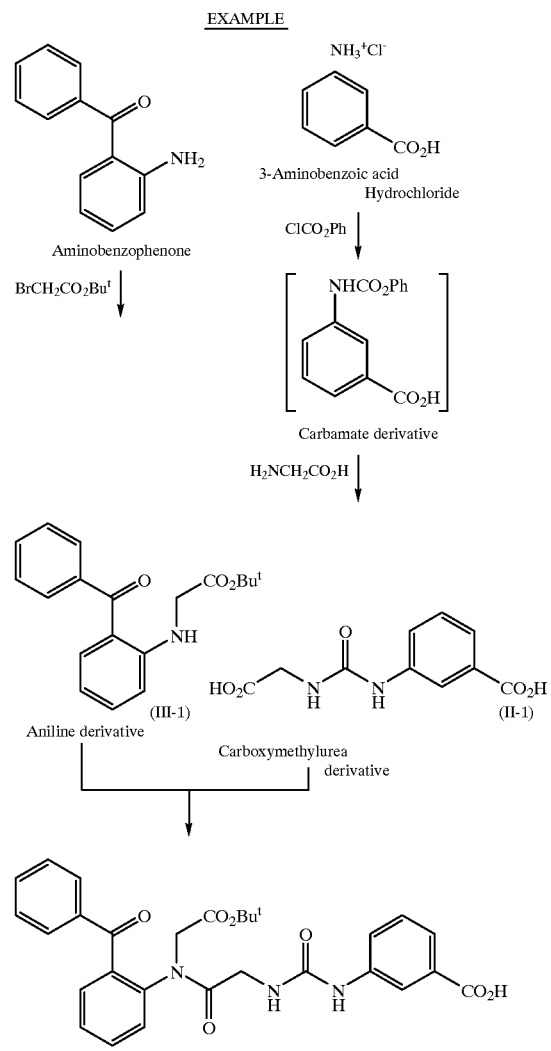

Example 1
Preparation of Carboxymethylurea Derivatives

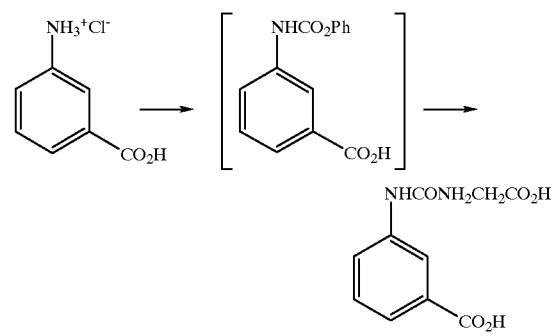

To a suspension of 3-aminobenzoic acid hydrochloride (25.0 g, 144 mmol) in water (125 ml) and acetonitrile(50 ml)

was added sodium hydrogencarbonate (54.4 g, 648 mmol) to dissolve the acid as sodium 3-aminobenzoate. To the solution was added dropwise phenyl chloroformate (24.8 g, 158 mmol) under ice-cooling and the mixture was stirred for 30 min under ice-cooling to give carbamate acid.

After the addition of glycine (16.2 g, 171 mmol), the mixture was stirred for 1 hr at 60° C. Phenol was extracted from the reaction mixture with ethyl acetate (2×). The aqueous layer was poured into conc. HCl (45 g, 432 mmol). The crystalline precipitates were filtered with suction, washed with water, and dried to yield 3-[3-(carboxymethyl)ureido]benzoic acid (30.9 g, yield 90%) as a white crystal. (Reference value, mp: 196–197° C., differential scanning calorimetric measurement (DSC).) $^1$H-NMR 200 MHz (d$_6$-DMSO) δ: 3.80 (d, J=5.8 Hz, 2 H), 6.40 (t, J=5.8 Hz, 1 H), 7.34 (t, J=7.8 Hz, 1 H), 7.49 (m, 1H), 7.60 (m, 1 H), 8.06 (t, J=1.8 Hz, 1 H)), 8.99 (s, 1 H).

Example 2
Preparation of Aniline Derivatives

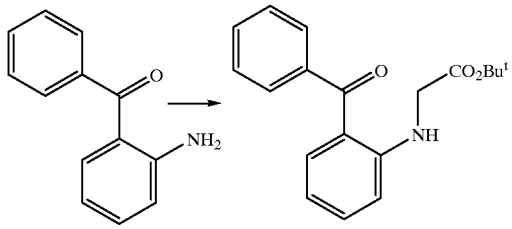

A mixture of 2-aminobenzophenone (20.00 g, 0.101 mol), potassium iodide (8.42 g, 0.0507 mol), potassium carbonate (21.02 g, 0.152 mol), N,N-dimethylformamide (30 ml) and t-butyl bromoacetate (29.67 g, 0.152 mol) was stirred at room temperature, and allowed to react at 80° C. for 5.5 hr. The mixture was cooled to give slurry, to which 40% aqueous methylamine solution (11.81 g, 0.152mol) was added to decompose excess t-butyl bromoacetate. To the mixture were added ethyl acetate (60 ml) and 6.4% hydrochloric acid (147 g, 0.259 mol) for partition. The ethyl acetate layer was washed once with 2.1% sodium hydrogencarbonate (41 g, 0.010 mol) and condensed under reduced pressure to remove the solvent. The residue was crystallized from n-hexane (70 ml) to yield 2-[N-(tert-butoxycarbonylmethyl)amino]benzophenone (27.41 g, yield 86.8%) as a yellow crystal. (Reference value, mp: 88° C. (DSC).) $^1$H-NMR 200 MHz (CDCl$_3$) δ: 1.50 (s, 9 H), 3.96 (d, J=5.3,2 H), 6.55–6.65 (m, 2H), 7.33–7.66 (m, 7H)), 8.90 (t, J=5.3,1 H)

Example 3
Preparation of Carbamoylmethylurea

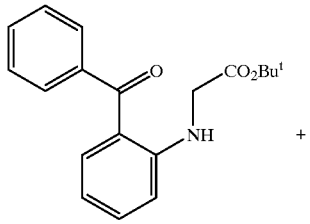

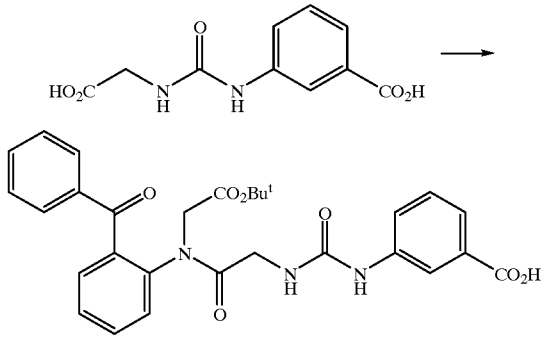

Carboxymethylurea derivative (28.6 g, 120 mmol) prepared in Example 1 was dissolved in N,N-dimethylformamide (74 ml) with stirring in a four-necked flask (200 ml). To the solution were added aniline derivative (24.5 g, 80 mmol) prepared in Example 2 and ethyl acetate (368 ml) and the mixture was cooled to −10° C. under a nitrogen atmosphere. Thionyl chloride (29.5 g, 248 mmol) was added dropwise over 30 min or more, and the mixture allowed to warm up to 5° C. and stirred for 3 hr. After the addition of water (74 ml), the mixture was stirred for 1 hr at room temperature. The organic layer was separated and washed twice with each of water (74 ml) and aqueous sodium hydrogencarbonate solution (74 ml), followed by extraction with aqueous sodium carbonate solution (pH 10) to obtain an aqueous layer containing the aimed product. The aqueous solution was extracted with ethyl acetate (123 ml) and aqueous sulfuric acid to separate the organic layer. The organic layer was washed with water and concentrated under reduced pressure to give slurry. Crude crystals were filtered off, washed with ethyl acetate (123 ml) and dried in vacuo to yield 2-[(tert-butoxycarbonylmethyl)-[3-(m-carboxyphenyl)ureidomethylcarbonyl]]aminobenzophenone (25.0 g, yield 58.9%, mp: 175–180° C.).

$^1$H-NMR (d$_6$-DMSO) δ: 1.37 (s, 9 H), 3.71 (ABqd, J=4.7,14.0Hz, 2 H), 3.95 (ABq, J=16.8 Hz, 2 H), 6.39 (bt, J=5.8 Hz, 1 H), 7.29~8.02 (m, 13 H)), 9.00 (s, 1 H).

What is claimed is:
1. A method for preparing a carbamoylmethylurea derivative of the formula (I):

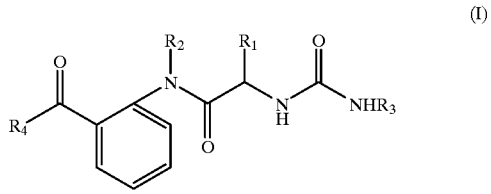

wherein R$_1$ is a hydrogen or lower alkyl; R$_2$ is a hydrogen or —CH$_2$COR$_5$ (R$_5$ is lower alkoxy, lower alkylamino, cycloalkyl, optionally substituted phenyl or optionally substituted heterocyclic group); R$_3$ is an optionally substituted phenyl; R$_4$ is an optionally substituted phenyl, optionally substituted cycloalkyl, optionally substituted alkyl or optionally substituted heterocyclic group, which comprises reacting a carboxymethylurea derivative of the formula (II):

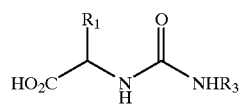
(II)

wherein R$_1$ and R$_3$ are as defined above or a reactive derivative thereof, with an aniline derivative of the formula (III):

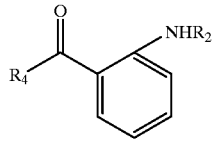
(III)

where R$_2$ and R$_4$ are as defined above.

2. The method of claim 1 wherein R$_2$ is —CH$_2$COR$_5$ (R$_5$ is as defined above.

3. The method of claim 1 wherein a carboxymethylurea derivative (II) or a reactive derivative thereof are reacted with an aniline derivative (III) in the presence of chlorination agent and N-substituted amide.

4. The method of claim 1 wherein R$_3$ is carboxyphenyl.

5. The method of claim 1 wherein a compound of the formula (II-1):

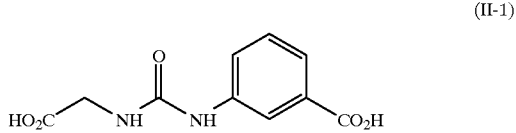
(II-1)

is reacted with a compound of the formula (III-1):

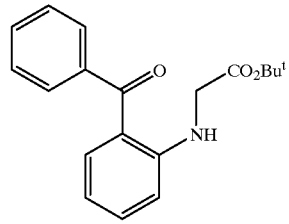
(III-1)

wherein Bu$^t$ is tert-butyl in the presence of SOCl$_2$ and dimethylformamide.

* * * * *